United States Patent [19]

Angevine et al.

[11] Patent Number: 4,600,503
[45] Date of Patent: Jul. 15, 1986

[54] PROCESS FOR HYDROTREATING RESIDUAL PETROLEUM OIL

[75] Inventors: Philip J. Angevine, West Deptford, N.J.; Thomas F. Degnan, Jr., Yardley, Pa.; Michael E. Landis, Woodbury, N.J.

[73] Assignee: Mobil Oil Corporation, New York, N.Y.

[21] Appl. No.: 774,520

[22] Filed: Sep. 10, 1985

Related U.S. Application Data

[63] Continuation-in-part of Ser. No. 687,414, Dec. 28, 1984.

[51] Int. Cl.$^4$ .................. C10G 17/00; C10G 45/00
[52] U.S. Cl. ...................... 208/251 H; 208/216 PP
[58] Field of Search ................ 208/251 H, 216 PP

[56] References Cited

U.S. PATENT DOCUMENTS

| | | | |
|---|---|---|---|
| 3,244,643 | 4/1966 | Schwartz | 502/64 |
| 3,865,895 | 2/1975 | Robson | 585/267 |
| 4,435,278 | 3/1984 | Chen | 208/251 H |
| 4,510,257 | 4/1985 | Lewis et al. | 502/63 |

*Primary Examiner*—Andrew H. Metz
*Assistant Examiner*—Helane Myers
*Attorney, Agent, or Firm*—A. J. McKillop; M. G. Gilman; L. P. Hobbes

[57] ABSTRACT

A method for hydrotreating residual oil which comprises utilizing a hydrotreating catalyst which contains a thermally stable composition comprising a layered metal oxide containing an interspathic polymeric oxide having a d-spacing of at least about 10 angstroms at hydrotreating conditions. Said conditions include temperature ranging from about 357° C. to 454° C. (675° F. to 850° F.), a hydrogen partial pressure of at least about 2860 kPa (400 psig) and a liquid hourly space velocity ranging between about 0.1 and 10 hr$^{-1}$.

18 Claims, No Drawings

PROCESS FOR HYDROTREATING RESIDUAL PETROLEUM OIL

This is a continuation-in-part of U.S. Ser. No. 687,414 filed Dec. 28, 1984, the entire contents of which are incorporated herein by reference.

This invention relates to a process of upgrading residual petroleum oils by hydrotreating. More particularly, the present invention relates to hydrotreating residual petroleum in the presence of a catalyst comprising a layered metal oxide component containing an interspathic polymeric oxide. This invention also relates to catalysts for hydrotreating residual petroleum oil, as well as methods of making the catalyst.

Residual petroleum oil fractions such as those heavy fractions produced by atmospheric and vacuum crude distillation columns, are typically characterized as being undesirable as feedstocks for most refining processes due primarily to their high metals, nitrogen, Conradson carbon residue and/or sulfur content. The presence of high concentrations of metals and sulfur and their compounds preclude the effective use of such residua as chargestocks for cracking, hydrocracking and coking operations as well as limiting the extent to which such residua could be used as fuel oil. Perhaps the single most undesirable characteristic of such feedstocks is their high metals content. Principal metal contaminants are nickel and vanadium. Sulfur is also undesirable in a process unit chargestock. The sulfur contributes to corrosion of the unit mechanical equipment and creates difficulties in treating products and flue gases. At typical cracking conversion rates, about one-half of the sulfur charged to the unit is converted to $H_2S$ gas which must be removed from the light gas product.

Increasingly, residual oil is being upgraded into lighter petroleum products, notably transportation fuels, by hydrotreating the residual oil. This treating of residual oil in the presence of a catalyst and hydrogen to transform it into lighter petroleum products is difficult because of the aforementioned presence of sulfur, nickel and vanadium in the molecules of the residual oil.

Catalysts having different size pores have been used to hydrotreat residual oil. For example, it has been recognized that large pore catalysts remove metals faster than small pore catalysts whereas small pore catalysts remove sulfur faster than large pores.

In the prior art, several catalysts, each having individual pore characteristics, have been employed to hydrotreat residual oils. For example, U.S. Pat. No. 4,054,508, teaches a process whereby a resid is passed over a large pore catalyst in order to demetallize the resid which is thereafter passed over a small pore desulfurizing catalyst. U.S. Pat. No. 4,267,071 teaches a hydrotreating catalyst whose pore size distribution is specifically tailored to complement the particular resid feed to be processed.

U.S. Pat. No. 4,389,304 discloses a hydrodesulfurization or hydrodenitrogenation catalyst containing alumina loaded with cobalt, molybdenum and titanium, while U.S. Pat. No. 4,287,050 discloses hydrodesulfurization with alumina promoted with zinc titanate, cobalt and molybdenum.

U.S. Pat. No. 3,865,895 discloses the use of layered complex metal silicates such as chrysotile in processes such as hydrodesulfurization and hydrodenitrogenation. However, the interlayer separation is relatively small for demetallation as is evidenced by d-spacings no greater than about 7.9 angstroms.

Because the principal metal contaminants such as nickel, vanadium, iron and copper are often associated with large planar organometallic complexes such as metalloporphyrins and similar cyclic tetrapyrroles, in the asphaltene fractions of resids, it would be particularly advantageous to employ a hydrotreating catalyst highly selective towards these shapes in resid upgrading. Such a material should exhibit not only hydrogenation activity, but also thermal stability such that the catalyst is capable of withstanding conditions ordinarily encountered during hydrotreating.

It has now been found that thermally stable layered metal oxides containing interspathic polymeric oxides may be employed in hydrotreating catalysts used to upgrade residual oil. Preferably, a hydrogenation component comprising metals selected from the group consisting of Group VIB and Group VIII is incorporated in the hydrotreating catalyst. The catalyst enhances removal of undesirable metals, sulfur, nitrogen and Conradson carbon residue.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van de Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the interlamellar spacing can be increased substantially by absorption of various swelling agents such as water, ethylene glycol, amines, ketones, etc., which enters the interlamellar space and push the layers apart. However, the interlamellar spaces of such layered materials tend to collapse when the molecules occupying the space are removed, for example, by exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

The method of the present invention may utilize a hydrotreating catalyst prepared from a layered oxide starting material which contains ion exchange sites having interspathic cations associated therewith. Such interspathic cations may include hydrogen ion, hydronium ion and alkali metal cation. The starting material is treated with a "propping" agent comprising a source of organic cation such as organoammonium ion in order to effect an exchange of the interspathic cations resulting in the layers of the starting material being propped apart. The source of organic cation in those instances where the interspathic cations include hydrogen or hydronium ions may include a neutral compound such as organic amine which is converted to a cationic analogue under such conditions. The organic cation should be capable of displacing or supplanting the original interspathic cations. The foregoing treatment results in the formation of a layered metal oxide of enhanced interlayer separation depending upon the size of the organic cation introduced.

After the ion exchange, the organic-"propped" species is treated with a compound capable of forming the above-described polymeric oxide. Preferably, such compounds are capable of forming the polymeric oxide upon hydrolysis. It is preferred that the organic cation deposited between the layers be capable of being removed from the layered oxide material without substantial disturbance or removal of the interspathic polymeric oxide. For example, organic cations such as n-octylammonium may be removed by exposure to calcination or chemical oxidation conditions, preferably after the interspathic polymeric oxide precursor has been converted to the polymeric oxide.

The polymeric oxide precursor-containing product is exposed to suitable conversion conditions, such as hydrolysis and/or calcination to form the layered material employed in the present invention. The hydrolysis step may be carried out by any method, for example, by interspathic water already present in organic-"propped" layered oxide material. Because of the effect of interspathic water on hydrolysis, the extent of hydrolysis may be modified by varying the extent to which the organic-"propped" species is dried prior to addition of the polymeric oxide precursor. As noted earlier, the product after conversion to the polymeric oxide form may be exposed to conditions which remove the organic cation propping agents, e.g., exposure to elevated temperature.

The amount of interspathic polymeric oxide contained within the final product can be greatly varied because the polymeric oxide precursor species are introduced in an electrically neutral form such that the amount of interspathic material incorporated within the layered oxide is not dependent upon the charge density of the original layered oxide. This allows the formation of materials with widely varying interlayer spacing, which permits accommodation of metal-containing molecules through the layered metal oxide.

The resulting product may have d-spacings greater than 10, 15, 20, 25 or even 30 angstroms. Layered oxides of elements ranging in atomic number from 13 to 15, 21 to 33, 39 to 51, 57 to 83 and greater than 90 may be employed as starting materials. Included amoung these materials are $KTiTaO_5$, and $Na_4Mn_{14}O_{27}\cdot 9H_2O$, as well as oxides of aluminum and silicon such as clays. Layered clays such as bentonite or layered silicates, for example, the metasilicates magadiite, natrosilite, kenyaite, maketite and kauemite, may be utilized as starting materials for the layered materials used in the present invention. It has been found preferable, or in some cases, necessary that these layered clays or silicates be treated by contacting with one or more polar solvents prior to or during exchange with the source of organic cation. The polar solvent used should exhibit electric dipole moments in the gas phase of at least 3.0 Debeyes (D), preferably at least 3.5 Debeyes, say at least about 3.8 D. Examples of suitable solvents are dimethylsulfoxide (DMSO) and dimethylformamide (DMF). The intercalation of synthetic magadiite with organic liquids such as DMSO, followed by treatment with alkylamines is discussed in *American Mineralogist,* Volume 60, pages 650–658, 1975, incorporated herein by reference. It is believed that the treatment of any starting material with one or more highly polar solvents can be useful in facilitating the introduction of the source of organic cation between the layers of starting material.

The layered metal oxide component used in the present invention may be prepared from starting materials such as layered oxides of Gr. IV A metals such as titanium, zirconium and hafnium. In particular, layered titanates, e.g., trititanates like $Na_2Ti_3O_7$ are useful starting materials. The starting materials comprise an interspathic cationic species between their layers. Trititanate is a commercially available material whose structure consists of infinite anionic sheets of titanium octahedra with intercalated alkali metal cations. The layered metal oxide component contains a stable polymeric oxide, preferably silica, between adjoining layers resulting in a heat-stable material which substantially retains its interlayer distance upon calcination. Silicotitanates employed in the present invention exhibit the characteristic x-ray diffraction pattern of Table 1 below.

TABLE 1

| Composite List of Principal X-Ray Powder* Diffraction Peaks For Silicotitanates | | |
|---|---|---|
| Line Number | $\left( \begin{array}{c} \text{2 Theta} \\ \text{Minimum} \end{array} - \begin{array}{c} \text{2 Theta} \\ \text{Maximum} \end{array} \right)$ | 100 $I/I_o$ (Relative Intensity) Range |
| 1 | less than or equal to 8.7 | VS to W |
| 2 | 11.1–14.3 | S to W |
| 3 | 11.8–15.2 | M to W |
| 4 | 24.5–25.0 | VS to W |
| 5 | 25.0–25.4 | M to W |
| 6 | 28.5–30.2 | VS to W |
| 7 | 29.8–30.6 | S to W |
| 8 | 33.0–33.5 | S to W |
| 9 | 43.2–43.5 | M to W |
| 10 | 44.2–44.7 | M to W |
| 11 | 48.5–48.9 | VS to M |
| 12 | 52.7–52.9 | W |

*2 Theta minimum − 2 Theta maximum = Range of 2 Theta-values observed for eight specific pillared silicotitanates These values were determined by standard techniques. The radiation was the K-alpha doublet of copper, and a scintillation counter spectrometer was used. The peak heights, I, and the positions as a function of 2 times theta, where theta is the Bragg angle, were determined. From these, the relative intensities, $I/I_o$ where $I_o$ is the intensity of the strongest line or peak, and d is the interplanar spacing in angstroms (A), corresponding to the recorded lines, were calculated. The relative intensity in the table above is expressed as follows:

| Relative Intensity | 100 I/Io |
|---|---|
| VS (Very Strong) | 60–100 |
| S (Strong) | 40–60 |
| M (Medium) | 20–40 |

| Relative Intensity | 100 I/Io |
|---|---|
| W (Weak) | 0–20 |

Variations in the interplanar spacing and relative intensity may occur as a result of ion exchange, changes in the composition of the silicotitanate, or exposure to calcination conditions.

The interspathic polymeric oxides formed between the layers of the layered oxide components of the present invention are preferably oxides of elements selected from Group IV B of the Periodic Table, including silicon, germanium, tin and lead, with silicon especially preferred. The polymeric oxide precursor may be an electrically neutral, hydrolyzable compound, such as tetrapropylorthosilicate, tetramethylorthosilicate, or preferably tetraethylorthosilicate. In addition, the polymeric oxide precursor may contain zeolite precursors such that exposure to conversion conditions results in the formation of interspathic zeolite material as at least some of the polymeric oxide.

The starting layered oxide material is treated with an organic compound capable of forming cationic species such as organophosphonium or organoammonium ion, before adding the polymeric oxide source. Insertion of the organic cation between the adjoining layers serves to separate the layers in such a way as to make the layered oxide receptive to the interlayer addition of the electrically neutral, hydrolyzable, polymeric oxide precursor. In particular, alkylammonium cations have been found useful in the present invention. $C_3$ and larger alkylammonium, e.g., n-octylammonium, is readily incorporated within the interlayer species of the layered oxides, serving to prop open the layers in such a way as to admit the polymeric oxide precursors. The extent of the interlayer spacing can be controlled by the size of the organoammonium ion employed. Indeed, the size and shape of the ammonium ion can affect whether or not the organoammonium ion can be interspathically incorporated within the layered oxide structure at all. For example, bulky cations such as tetrapropylammonium are not particularly suited to the present invention.

The organic ammonium cation precursor may be formed by combining a precursor amine and a suitable acid, e.g. mineral acids such as hydrochloric acid. The layered oxide starting material can then be combined with the resulting aqueous solution of ammonium ion to form a layered oxide containing intercalated organic material and water. The resulting "propped" product is then contacted with an electrically neutral, hydrolyzable polymeric oxide precursor. After hydrolysis, preferably by exposure to interspathic water, the polymeric oxide precursor forms a thermally stable polymeric oxide. A final calcination step may be employed which is severe enough to remove the organic interspathic species. Remaining organic may also be removed, if desired, by a separate chemical treatment.

Layered metal oxides containing an interspathic polymeric oxide such as those described above have now been found to be useful in upgrading residual oil, particularly in demetallation by hydrotreating. The layered materials useful in the method of the present invention preferably exhibit significant interlayer separation and possess a d-spacing of at least about 10 angstroms. The interspathic polymeric oxide serves to adequately maintain the interlayer separation even at the conditions of temperature and pressure encountered during resid upgrading. The layered metal oxides described above are particularly useful in resid upgrading catalysts because their layered structure results in pores which are relatively long and narrow. Such pore shapes are believed to readily accomodate all or part of the large planar metal complexes found in asphaltene portions of resid and thus permit access of such metal complexes to catalytic sites within the catalysts.

The present invention relates to a method for hydrotreating 350° C.+ and preferably 540° C.+ residual oil which comprises utilizing a hydrotreating catalyst which contains a thermally stable composition comprising a layered metal oxide containing an interspathic polymeric oxide having a d-spacing of at least about 10 angstroms, 15 angstroms, or 20 angstroms under hydrotreating conditions.

The present invention may also relate to a method for removing metal from a metal-containing residual oil by hydrotreating. The residual oil is contacted with hydrogen in the presence of a hydrotreating catalyst comprising a layered metal oxide containing an interspathic polymeric oxide having a d-spacing of at least about 10 angstroms. Preferably, the hydrotreating catalyst contains a metal selected from the group consisting of group VIB and Group VIII metals. Preferably, the hydrotreating catalyst comprises a layered silicotitanate. The metals removed from the residual oil may include such common crude oil metal contaminants as nickel, vanadium, iron, copper, zinc and sodium, and are often in the form of large organometallic complexes such as metal porphyrins or asphaltenes.

The residual feedstock employed in the present invention will normally be substantially composed of residual hydrocarbons boiling above 340° C. and containing a substantial quantity of asphaltic materials. Thus the chargestock can be one having an initial or 5 percent boiling point somewhat below 340° C. provided that a substantial proportion, for example, about 70 or 80 percent by volume, of its hydrocarbon components boil above 340° C. A hydrocarbon stock having a 50 percent boiling point of about 480° C. and which contains asphaltic materials, 4 percent by weight sulfur and 50 p.p.m. nickel and vanadium is illustrative of such chargestock.

The process of the present invention may be carried out by contacting a metal and/or sulfur contaminated feedstock with the above-described hydrotreating catalyst under hydrogen pressures of at least about 2860 kPa (400 psig), temperatures ranging between about 357° to 454° C. (675° to 850° F.) and liquid hourly space velocities between about 0.1 and 10 hr$^{-1}$. Preferably these conditions include hydrogen pressures between about 7000 to 17000 kPa (about 1000 to 2500 psig), temperatures between about 370° to 440° C. (about 700° to 825° F.), and liquid hourly space velocities between about 0.2 and 1.0 hr$^{-1}$.

The catalytic hydrotreating may take place in any suitable hydrotreating reactor, preferably a fixed bed downflow (trickle bed) reactor. Other suitable hydrotreaters include moving bed downflow ("bunker") reactors, fluidized bed or ebullated bed reactors and fixed bed upflow reactors.

The use of the present hydrotreating catalysts in resid upgrading is particularly desirable because they exhibit greater activity, particularly in metals removal. Accordingly a refiner can attain the required degree of metals removal with less catalyst in a smaller reactor. In view of the high pressures required for hydroprocessing resids, it is highly desirable from an economic standpoint to utilize a reactor of the smallest size allowable. Alternatively, hydrotreating with the catalysts of the present method in larger reactors allows a refiner to operate at lower reaction severities or to attain hydrotreated resids of improved quality. In view of this, the method of the present invention is believed particularly useful in pretreating FCC feed or producing metallurgical grade coke.

The following examples are given to further describe the present invention.

EXAMPLE 1

Preparation of Reference CoMo/Al$_2$O$_3$, Catalyst A

The support for reference catalyst A was prepared by extruding a mixture of water and alpha alumina monohydrate ("Catapal SB") to 1/32" extrudate, drying at about 140° C., and calcining at a particular temperature to give a distinct pore size distribution. The calcined extrudate was then sequentially impregnated via the incipient wetness technique with ammonium heptamolybdate and cobalt chloride. Drying at about 140° C. and calcination at 540° C. followed each of the two impregnations. Properties of the resultant Catalyst A are shown in Table 2.

TABLE 2

| CoMo/Al$_2$O$_3$ Resid Demetalation Catalyst Properties | |
|---|---|
| Metals Loading (wt %) | |
| CoO | 3.5 |
| MoO$_3$ | 10.0 |
| Physical Properties | |
| Surface Area, m$^2$/g | 109 |
| Real Density, g/cc | 3.629 |
| Particle Density, g/cc | 1.221 |
| Pore Volume, cc/g | 0.543 |
| Avg. Pore Dia., Ang. | 199 |
| PSD, % PV in Pores of | |
| 0–30 Ang. Diameter | 11 |
| 30–50 | — |
| 50–80 | — |
| 80–100 | 2 |
| 100–150 | 24 |
| 150–200 | 34 |
| 200–300 | 17 |
| 300+ | 12 |

EXAMPLE 2

Preparation of H$_2$Ti$_3$O$_7$

Acid titanate, H$_2$Ti$_3$O$_7$, was prepared from exchange of Na in Na$_2$Ti$_3$O$_7$ with 1 M HCl in triplicate as described: 780.7 g 37.4% HCl was diluted to 8 liters total volume with water in a 12 liter 4-necked round bottom flask equipped with a mechanical stirrer, reflux condenser, and thermometer. 500 Grams of Na$_2$Ti$_3$O$_7$ were added, and the resulting mixture was heated with stirring at 75°–80° C. for 24 hours. The solution was then filtered and washed with 2 liters of hot water. The procedure was repeated in triplicate. After the third exchange, the product was washed with hot water until chloride free. The product after drying in vacuo at 77° C. had an X-ray diffraction pattern similar to that reported for H$_2$Ti$_3$O$_7$ by H. Izawa, S. Kikkaw, and M. Kolzumi, J. Phys. Chem., 86,5023 (1982) and the following composition (wt %).

TiO$_2$, 93.4

Na, 0.28

EXAMPLE 3

Preparation of Silicotitanate

Concentrated HCl (315.6 g of 37.2% HCl) was dissolved in 700 g water, and the resulting solution was stirred and cooled in an ice bath. n-Octylamine (427.1 g) was added portionwise, keeping the solution below 50° C. 100 grams of Na$_2$Ti$_3$O$_7$ was added, and the mixture was transferred to a 2 liter polypropylene jar and heated at 100° C. with occasional stirring for 24 hours. The mixture was filtered, washed with 5 liters hot water, and dried at room temperature for 24 hours. A portion of this dried product (90 g) was stirred in 600 g tetraethylosthiosilicate for 72 hours at room temperature, filtered, and dried at room temperature for 24 hours. This product was calcined at 1000° F. in nitrogen for one hour and in air for 2 hours. The properties of this silicotitanate product are provided in Table 3.

TABLE 3

| Properties of Catalyst A Silicotitanate of Example 3 | |
|---|---|
| SiO$_2$/TiO$_2$, molar | 0.52 |
| Na, wt % | 2.80 |
| Ash, wt % | 98.45 |
| Surface Area, m$^2$/g | 225.00 |
| Sorption, wt % | |
| H$_2$O | 10.6 |
| Cyclohexane | 7.6 |
| n-Hexane | 6.1 |

EXAMPLES 4–6

EXAMPLE 4

Preparation of Molybdenum-Containing Titanate, Catalyst B

A Mo/Na$_2$Ti$_3$O$_7$ material was prepared by the conventional incipient wetness technique on sodium titanate using ammonium heptamolybdate. Following impregnation of 10 wt % MoO$_3$, the material was calcined in air at 800° F. for 3 hours. The resultant catalyst was identified as catalyst B.

EXAMPLE 5

Preparation of Molybdenum-Containing Titanate, Catalyst C

Using the acid titanate produced from Example 2, a Mo impregnation and calcination similar to Example 4 were completed. The finished material was identified as Catalyst C.

EXAMPLE 6

Preparation of Molybdenum-Containing Titanate, Catalyst D

Using the silicotitanate of Example 3, a Mo impregnation and calcination similar to Examples 4 and 5 were completed. The finished material was identified as Catalyst D.

Properties of Catalysts B, C, and D are set out in Table 4.

TABLE 4

| Properties of Molybdenum-Containing Titanate Catalysts | | | |
|---|---|---|---|
| | Catalyst B | Catalyst C | Catalyst D |
| Form | Mo— Impregnated Na$_2$Ti$_3$O$_7$ | Mo— Impregnated H$_2$Ti$_3$O$_7$ | Mo— Impregnated Silicotitanate |

TABLE 4-continued

Properties of Molybdenum-Containing Titanate Catalysts

|  | Catalyst B | Catalyst C | Catalyst D |
|---|---|---|---|
|  | 8/20 Mesh Particles | 8/20 Mesh Particles | 8/20 Mesh Particles |
| Density, g/cc Packed | 0.57 | 0.54 | 0.59 |
| Pore Volume cc/g | NA | NA | 0.497 |
| Surface Area $M^2/g$ | 5 | 5 | 45 |
| Avg. Pore diameter, Ang. | NA | NA | 442 |
| % Pore Volume in Pores of Varying Diameters (angstroms) | | | |
| 0-30 Ang. Diameter | | | 1 |
| 30-50 Ang. Diameter | | | 1 |
| 50-80 Ang. Diameter | | | 2 |
| 80-100 Ang. Diameter | | | 3 |
| 100-150 Ang. Diameter | | | 2 |
| 150-200 Ang. Diameter | | | 3 |
| 200-300 Ang. Diameter | | | 3 |
| 300+ Ang. Diameter | | | 87 |

EXAMPLE 7

Shaker Bomb Testing of Catalysts of A, B, C & D Using Arab Light Vacuum Resid

The catalysts of Examples 1, 4, 5, and 6 all crushed and sized to a log means particle diameter of 14 to 20 Mesh (Tyler) were employed in hydrotreating an Arabian Light vacuum resid (540° C.+ boiling range) described in Table 5 in a shaker bomb apparatus (see J. W. Payne, C. W. Streed and E. R. Kent, "The Shaker Bomb - A New Laboratory Tool for Studying Thermal Processes", Ind. Eng. Chem., 50 (1), 47 (1958)) which approximates resid upgrading activities observed in continuous downflow units.

TABLE 5

| Arabian Light Vacuum Resid Feedstock | |
|---|---|
| Elemental Analysis (wt %) | |
| Hydrogen | 10.68 |
| Sulfur | 3.93 |
| Nitrogen | 0.31 |
| CCR | 16.96 |
| Asphaltenes (n-$C_5$) | 10.93 |
| Metals Analysis (ppm) | |
| Nickel | 16 |
| Vanadium | 65 |
| Iron | 12 |
| Sodium | 6 |
| Kinematic Viscosity (cs) | |
| 212° F. | 496.2 |
| 300° F. | 24.6 |

In a series of runs, the titanate catalysts were contacted with the resid at the following conditions:

| | |
|---|---|
| Oil:Catalyst (Wt:Wt) | 20 |
| Temperature, °C. | 400 |
| $H_2$ Pressure, kPa | 13,890 |
| Reaction Time, min | 80 |

At the conclusion of each run, the catalyst and the oil were separated and both components were analyzed. The effectiveness of each catalyst for resid upgrading was determined by comparing the degree of demetalation, desulfurization, CCR removal, and denitrogenation to that observed in an identical run in which a conventional CoMo/$Al_2O_3$ catalyst was used. Thermal contributions were determined from a "blank" run at identical conditions but with no catalyst present.

Table 6 presents the results of this catalyst activity comparison and shows that the molybdenum-impregnated silicotitanate catalyst was superior to the analogously treated sodium titanate and hydrogen titanate, catalysts with respect to CCR, vanadium, and asphaltenes removal. Sulfur removal by all three titanate catalysts was minimal. This was expected since unpromoted $MoO_3$ is known to have little desulfurization activity. Nickel levels in the sodium and hydrogen titanate treated products actually increased due to contamination that can be traced to the stainless steel walls of the shaker bomb. The demetalation activity of the silicotitanate was sufficient to take up this additional nickel.

TABLE 6

Comparison of Resid Upgrading Catalyst Performance

| | Thermal | Catalyst A (CoMo/Al) | Catalyst B (Mo/Sodium Titanate) | Catalyst C (Mo/Hydrogen Titanate) | Catalyst D (Mo/Silico Titanate) |
|---|---|---|---|---|---|
| Conditions | | | | | |
| Temp, °C. | 400 → | → | → | → | → |
| Pressure, kPa | 13,890 → | → | → | → | → |
| Oil/Cat (wt %) | Inf. | 20 → | → | → | → |
| Time, min | 80 → | → | → | → | → |
| Conversion to 540° C.-, wt % | 13.0 | 32.7 | 4.0 | 17.0 | 24.0 |
| Total Liquid Product Analysis, wt % | | | | | |
| Hydrogen | 10.58 | 10.88 | 10.24 | 10.26 | 10.22 |
| Sulfur | 3.47 | 2.52 | 3.96 | 3.87 | 3.87 |
| Nitrogen | 0.32 | 0.26 | 0.26 | 0.26 | 0.26 |
| Vanadium, ppm | 70 | 33 | 62 | 62 | 24 |
| Nickel, ppm | 16 | 10 | 18 | 19 | 12 |
| CCR, wt % | 16.00 | 14.44 | 16.46 | 16.04 | 16.37 |
| Asphaltenes wt % Removal, % | 8.52 | 5.40 | 6.99 | 9.76 | 5.56 |

TABLE 6-continued

Comparison of Resid Upgrading Catalyst Performance

|  | Thermal | Catalyst A (CoMo/Al) | Catalyst B (Mo/Sodium Titanate) | Catalyst C (Mo/Hydrogen Titanate) | Catalyst D (Mo/Silico Titanate) |
| --- | --- | --- | --- | --- | --- |
| Vanadium | 0 | 49 | 5 | 5 | 63 |
| CCR | 6 | 15 | 3 | 6 | 3 |
| Sulfur | 12 | 36 | 0 | 2 | 2 |
| Asphaltenes | 22 | 51 | 36 | 11 | 49 |

Compared to the conventional CoMo/Al$_2$O$_3$ catalyst, Mo/silicotitanate has greater demetalation activity (63 percent vs. 49 percent). Asphaltene removal activities of the two catalysts are virtually equivalent (49 percent vs 51 percent).

It is claimed:

1. A method for hydrotreating residual oil which comprises contacting said oil with a hydrotreating catalyst which contains a thermally stable composition comprising a layered metal oxide containing an interspathic polymeric oxide having a d-spacing of at least about 10 angstroms, at hydrotreating conditions which include a temperature ranging from about 357° C. to 454° C. (675° F. to 850° F.) a hydrogen partial pressure of at least about 2860 kPa (400 psig) and a liquid hourly space velocity ranging between about 0.1 and 10 hr$^{-1}$.

2. The method of claim 1 wherein said hydrotreating catalyst contains a Group VIB metal selected from the group consisting of chromium, molybdenum and tungsten.

3. The method of claim 2 wherein said hydrotreating catalyst contains a Group VIII metal.

4. The method of claim 3 wherein said group VIII metal is selected from the group consisting of iron, cobalt, nickel, palladium and platinum.

5. The method of claim 1 wherein said layered metal oxide component containing an interspathic polymeric oxide is a silicotitanate.

6. The method of claim 1 wherein said d-spacing is at least about 15 angstroms.

7. The method of claim 6 wherein said d-spacing is at least about 20 angstroms.

8. The method of claim 1 wherein said hydrotreating occurs in a fixed bed downflow reactor.

9. The method of claim 5 wherein said hydrotreating catalyst contains molybdenum.

10. The method of claim 5 wherein said hydrotreating catalyst contains cobalt.

11. The method of claim 5 wherein said hydrotreating catalyst contains molybdenum and cobalt.

12. The method of claim 5 wherein said hydrotreating catalyst contains nickel.

13. The method of claim 5 wherein said hydrotreating catalyst contains tungsten.

14. The method of claim 5 wherein said hydrotreating catalyst contains nickel and tungsten.

15. The method of claim 5 wherein said hydrotreating conditions include a temperature ranging from about 370° C. to 440° C. (700° F. to 825° F.), a hydrogen partial pressure ranging from about 7000 to 17,000 kPa (1000 to 2500 psig), and a liquid hourly space velocity ranging between about 0.2 to 1.0.

16. A method for removing metal from a metal-containing residual oil which comprises hydrotreating said residual oil with a hydrotreating catalyst comprising a layered silicotitanate wherein said catalyst contains a Group VIB metal, at a temperature ranging from about 357° C. to 454° C. (675° F. to 850° F.), a hydrogen partial pressure of at least about 2860 kPa (400 psig) and a liquid hourly space velocity ranging between about 0.1 and 10 hr$^{-1}$.

17. The method of claim 16 wherein said metal removed is vanadium.

18. The method of claim 16 wherein said metal removed is nickel.

* * * * *

UNITED STATES PATENT AND TRADEMARK OFFICE
CERTIFICATE OF CORRECTION

PATENT NO. : 4,600,503
DATED : July 15, 1986
INVENTOR(S) : Philip J. Angevine, Thomas F. Degnan, Jr. and Michael E. Landis It is certified that error appears in the above-identified patent and that said Letters Patent is hereby corrected as shown below:

Column 9, line 16, after "80-100 Ang. Diameter" delete "3" and insert --2--.

Column 9, line 17, after "100-150 Ang. Diameter" delete "2" and insert --3--.

Column 9, line 18, after "150-200 Ang. Diameter" delete "3" and insert --2--.

Signed and Sealed this

Fifteenth Day of September, 1987

*Attest:*

DONALD J. QUIGG

*Attesting Officer*     *Commissioner of Patents and Trademarks*